United States Patent [19]

Migita et al.

[11] Patent Number: 4,686,292

[45] Date of Patent: Aug. 11, 1987

[54] BENZO[α]PHENAZINE ANTITUMOR AGENTS

[75] Inventors: Yoshihiro Migita, Ina; Tadashi Eguchi; Yukinari Kumazawa, both of Ohmiya; Jozi Nakagami, Ina; Takehiro Amano, Urawa; Kaoru Sota, Tokorozawa; Jinsaku Sakakibara, Nagoya, all of Japan

[73] Assignee: Taisho Pharmaceutical Co., Ltd., Japan

[21] Appl. No.: 838,153

[22] Filed: Mar. 10, 1986

[30] Foreign Application Priority Data

Mar. 29, 1985 [JP] Japan ................................ 60-65099

[51] Int. Cl.⁴ ................. A61K 31/495; C07D 241/46; C07D 403/06; C07D 401/06
[52] U.S. Cl. .......................................... 544/343
[58] Field of Search ........................................ 544/343

[56] References Cited

PUBLICATIONS

"Studies on Antitumor Activity of Phenazine Derivatives Against S 180 in Mice (VIII)," Hideo Endo, Masao Tado and Ken Katagiri, *Sci. Rep. Res. Inst. Tohoku Univ.*-C, vol. 16, No. 1–2, 1969, pp. 18–26.
Taisho, Chem. Abs. 101, 90980a (1984).

*Primary Examiner*—Mark L. Berch
*Attorney, Agent, or Firm*—Pahl, Lorusso & Loud

[57] ABSTRACT

Novel benzo[α]phenazine derivatives of the formula

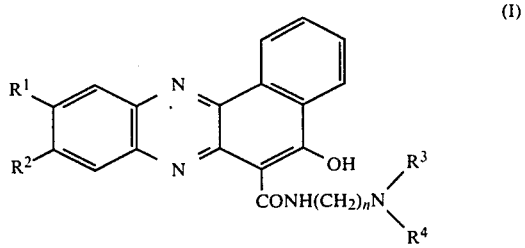

(I)

wherein $R^1$ is hydrogen, halogen, methyl, hydroxyl or alkoxy, $R^2$ is $—COOR^5$ (wherein $R^5$ is hydrogen, straight or branched chain alkyl, cycloalkyl having 3–6 carbon atoms, benzyl or phenyl) or

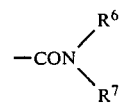

wherein $R^6$ and $R^7$ are the same or different and are each hydrogen or lower alkyl, or $R^6$ and $R^7$ together with the nitrogen atom to which they are attached form pyrrolidine or piperidine), $R^3$ and $R^4$ are the same or different and are each hydrogen or lower alkyl, and n is an integer of 2 or 3, and the salts thereof are disclosed. These compounds have antitumor activity in mammals.

6 Claims, No Drawings

BENZO[α]PHENAZINE ANTITUMOR AGENTS

The present invention relates to novel benzo[α]-phenazine derivatives useful for ameliorating cancer diseases in mammals.

Some benzo[α]phenazine derivatives having antitumor activity have been disclosed in Science Reports of the Research Institute of Tohoku University -C, Vol. 16, No. 1-2, page 18–26 (1969). However, these known compounds are not satisfactory for activity.

As a result of studies on benzo[α]phenazines having a carboxamide group at the 5-position, the inventors have found novel derivatives showing excellent antitumor activity on transplanted mouse tumors, and the present invention have been completed.

The present invention relates to benzo[α]phenazine derivatives of the formula

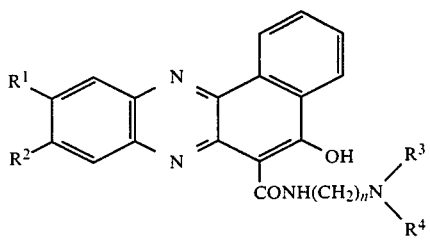
(I)

wherein $R^1$ is hydrogen, halogen, methyl, hydroxyl or alkoxy, $R^2$ is —COOR$^5$ (wherein $R^5$ is hydrogen, straight or branched chain alkyl, cycloalkyl having 3–6 carbon atoms, benzyl or phenyl) or

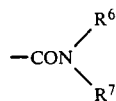

(wherein $R^6$ and $R^7$ are the same or different and are each hydrogen or lower alkyl, or $R^6$ and $R^7$ together with the nitrogen atom to which they are attached form pyrrolidine or piperidine), $R^3$ and $R^4$ are the same or different and are each hydrogen or lower alkyl, and n is an integer of 2 or 3, and the salts thereof.

In the present invention, the term "halogen" refers to fluorine, chlorine, bromine or iodine, the term "alkoxy" refers to lower alkoxy such as methoxy, ethoxy, propoxy, butoxy and the like, the term "straight or branched chain alkyl" refers to the alkyl having 1 to 20 carbon atoms such as methyl, ethyl, propyl, isopropyl, butyl, isobutyl, pentyl, neopentyl, hexyl, decyl, eicosyl and the like, and the term "lower alkyl" refers to methyl, ethyl, propyl, butyl and the like. The term "salt" of the compound of formula I includes pharmaceutically acceptable salts of inorganic acids such as hydrochloric acid, sulfuric acid and the like, and organic acids such as acetic acid, propionic acid, butyric acid, oxalic acid, malic acid, malonic acid, fumaric acid, benzoic acid, toluic acid and the like, which are prepared by treating the compound of formula I with the corresponding acid. In case of the compound of formula I wherein $R^2$ is COOH, these salts also include the above acid salts and salts of sodium, potassium, calcium and the like, which are prepared by treating the compound of formula I or the acid salts thereof with the corresponding metal base.

Preferred compounds of formula I are those wherein R wherein $R^1$ is alkoxy, $R^2$ is —COOR$^5$ (wherein R5 is hydrogen or alkyl), $R^3$ and $R^4$ are each methyl and n is an integer of 2.

The compound of formula I can be prepared as follows: namely, a heterocyclic compound of the formula

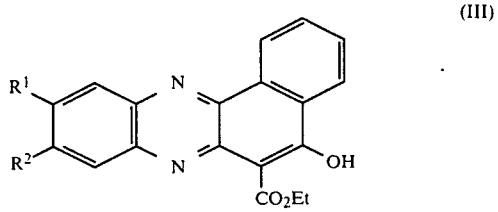
(III)

wherein $R^1$ and $R^2$ are as defined above, is condensed with an alkylamine of the formula

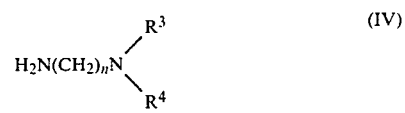
(IV)

wherein $R^3$, $R^4$ and n are as defined above to give the compound of formula I. This condensation is carried out in the absence or presence of an organic solvent such as benzene, toluene, N,N-dimethylformamide, ethanol, dichloromethane, tetrahydrofuran and the like. The reaction temperature is 10° to 120° C., preferably 15° to 30° C. In case where long reaction time is required, it is preferable to raise the reaction temperature or to add an alkali catalyst such as sodium alkoxide in order to shorten the reaction time.

A compound of formula I wherein $R^2$ is COOH may be converted, by esterification with a diazoalkane which can form desired group of alkyl for $R^5$, into the different compound of formula I wherein $R^2$ is COOR$^5$ wherein $R^5$ is alkyl.

A compound of formula I wherein $R^2$ is COOR $^5$ wherein $R^5$ is alkyl may be converted, by transesterification with an alcohol which can form desired alkyl group for $R^5$ in an acidic catalyst (e.g., sulfuric acid, p-toluenesulfonic acid and the like), into a different compound of formula I wherein $R^5$ is alkyl.

A compound of formula I wherein $R^2$ is COOR$^5$ wherein $R^5$ is other than hydrogen can be converted, by alkali hydrolysis in a solvent (e.g., water, alcohol, N,N-dimethylformamide, dimethyl sulfoxide, a mixture thereof, and the like), into a different compound of formula I wherein $R^5$ is hydrogen.

A compound of formula I wherein $R^2$ is COOR$^5$ wherein $R^5$ is alkyl can be converted, by aminolysis using ammonia or a corresponding primary amine in an organic solvent (e.g., dioxane, chloroform and the like) or in the absence of solvent under atmospheric pressure or in sealed tube, into a different compound of formula I wherein $R^2$ is

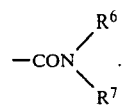

The compound of formula III can be prepared by treating ethyl 3-hydroxy-1,4-dihydro-1,4-dioxo-2-naphthoate with N,N'-carbonyldiimidazole, an acyl chloride (e.g., acetyl chloride, pivaloyl chloride and the like) or a chloroformate (e.g., ethyl chloroformate, benzyl chloroformate and the like) in an organic solvent (e.g., tetrahydrofuran, N,N-dimethylformamide, dioxane and the like), followed by condensation of the resulting compound with a phenylenediamine of the formula

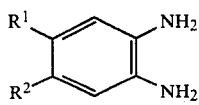 (II)

wherein $R^1$ and $R^2$ are as defined above.

When treated with an acyl chloride or a chloroformate, it is convenient to use a basic catalyst such as trietylamine, pyridine and the like.

Some of phenylenediamines of formula II are known and some are new. The latter may be prepared by methods known per se. For example, 5-acetylamino salicylic acid is subjected to O-alkylation, nitration, deacetylation and reduction, successively, to obtain the desired phenylenediamine of formula II. Thus obtained phenylenediamines can be preferably used for the above condensation without purification.

The compounds of formula I showed antitumor activity on transplanted mouse tumors and are useful for regression or palliation of leukemia in mammals. For the purposes, they may be administered orally, parenterally or locally in conventional dosage forms such as tablets, powders, capsules, solutions, suspensions, emulsions, suppositories and the like, all of which are prepared according to conventional pharmaceutical practices.

The effective dosage of the compounds of formula I depends on the age, weight or response of patient. Generally, however, the daily dosage may range from 0.1 to 10 mg/kg.

The following test shows the antitumor activity on transplanted mouse tumors.

P388 lymphocytic leukemia test

The animals used are 5-6 weeks old $CDF_1$ female mice weighing 17-20 g. The animals were intraperitoneally transplanted with $1 \times 10^6$ cells of P388 lymphocytic leukemia passaged on DBA/2 female mice on day 0. A suspension of the compound of formula I in 0.5 % gum arabic saline solution was administered intraperitoneally once a day, 5 times in all, from day 1 to day 5. A solution of 5-fluorouracil in saline served as reference drug, and was administered similarly. Control group were similarly administered with only 0.5 % gum arabic saline solution. Eight animals were used for the treated group with the compound I and the reference drug, respectively, and 16 animals for control group. The activity was evaluated according to the screening system of the National Cancer Institute of the United States. The survivors of animals were recorded on a regular basis for 30 days, and the value of T/C×100 (%) was calculated from the medium survival times for the treated animals (T) and the control animals (C). Drugs producing a value of T/C×100 more than 125 were judged to be active against P388 lymphocytic leukemia.

The results of the test are shown in Table 1. The compounds of the present invention were effective in the wide range of dosages.

TABLE 1

| Compound | Doses (mg/Kg) | T/C × 100 |
|---|---|---|
| A | 100 | 90 |
|   | 50 | 588 |
|   | 25 | 183 |
|   | 12.5 | 172 |
|   | 6.25 | 154 |
|   | 3.13 | 151 |
|   | 1.6 | 132 |
|   | 0.8 | 127 |
| B | 200 | 80 |
|   | 100 | 300 |
|   | 50 | 300 |
|   | 25 | 280 |
|   | 12.5 | 280 |
|   | 6.25 | 203 |
|   | 3.13 | 173 |
|   | 1.6 | 170 |
|   | 0.8 | 167 |
|   | 0.4 | 161 |
|   | 0.2 | 160 |
|   | 0.1 | 132 |
| 5-Fluorouracil | 50 | 87 |
|   | 25 | 176 |
|   | 12.5 | 167 |
|   | 6.25 | 148 |
|   | 3.13 | 136 |
|   | 1.6 | 125 |
|   | 0.8 | 112 |

(Note)
Compound A = N—β-Dimethylaminoethyl 5-hydroxy-10-methoxy-9-methoxycarbonylbenzo[α]phenazine-6-carboxamide
Compound B = N—β-Dimethylaminoethyl 9-carboxy-5-hydroxy-10-methoxybenzo[α]phenazine-6-carboxamide The present invention is further illustrated by the following Referential Examples and Examples.

REFERENTIAL EXAMPLE 1

Ethyl 5-acetylamino-2-ethoxybenzoate,

To 300 ml of acetone were added 20 g of 5-acetylaminosalicylic acid, 41 ml of ethyl iodide and 50.5 g of anhydrous potassium carbonate, and then the mixture was refluxed for 24 hours. After cooling, the insoluble was removed by filtration, the filtrate was evaporated to dryness under reduced pressure, and the residue was recrystallized from diethyl ether to give the title compound, m.p 78°-79° C., yield of 13.68 g.

REFERENTIAL EXAMPLE 2

Ethyl 5-acetylamino-2-ethoxy-4-nitrobenzoate

To a stirred suspension of 13.06 g of ethyl 5-acetylamino 2-ethoxybenzoate in 50 ml of acetic anhydride was added dropwise 3 ml of fuming nitric acid under ice cooling. After completion of the addition, the mixture was stirred under ice cooling for 30 minutes then at room temperature for 4 hours. The reaction solution was poured into an ice water, the resulting crystals were collected by filtration and recrystallized from ethanol to give the title compound, m.p. 118°-120° C., yield of 6 35 g.

REFERENTIAL EXAMPLE 3

Methyl 5-amino-2-ethoxy-4-nitrobenzoate

A suspension of 1 5 g of ethyl 5-acetylamino-2-ethoxy-4-nitrobenzoate in 50 ml of 5 % (v/v) sulfuric acid methanolic solution was refluxed for 4 hours After cooling, the reaction solution was poured into an ice water, the resulting crystals were collected by filtration and recrystallized from methanol to give the title compound, m.p. 156°-157° C., yield of 1.01 g.

REFERENTIAL EXAMPLE 4

Ethyl 10-ethoxy-5-hydroxy-9-methoxycarbonylbenzo[α]- phenazine-6-carboxylate (1) A suspension of 873 mg of methyl 5-amino-2-ethoxy-4-nitrobenzoate and 50 mg of 10 % palladium carbon in 50 ml of ethanol was stirred at room temperature under a hydrogen atmosphere. After the absorption of hydrogen was completed, the catalyst was removed by filtration, and the filtrate was evaporated to dryness under reduced pressure to give crude methyl 4,5-diamino-2-ethoxybenzoate.

(2) To a solution of 895 mg of ethyl 3-hydroxy-1,4-dihydro1,4-dioxo-2-naphthoate in 10 ml of N,N-dimethylformamide was added 620 mg of N,N'-carbonyldiimidazole, and the mixture was stirred at room temperature for 2 hours. To the mixture was added the crude methyl 4,5-diamino-2-ethoxybenzoate in 10 ml of N,N-dimethyl-formamide under ice cooling, and the mixture was stirred at room temperature overnight. To the reaction solution was added 200 ml of ethanol, and then the resulting precipitate was collected by filtration and recrystallized from chloroform - ethanol to give the title compound, m.p. 270°–273° C., yield of 531 mg.

REFERENTIAL EXAMPLE 5

By the procedure of Referential Example 1 the following compounds were obtained using the corresponding alkyl iodides
Propyl 5-acetylamino-2-propoxybenzoate as an oil
Butyl 5-acetylamino-2-butoxybenzoate as an oil

REFERENTIAL EXAMPLE 6

By the procedure of Referential Example 2 the following compounds were obtained using the corresponding acetylamino- benzoates.
Propyl 5-acetylamino-4-nitro-2-propoxybenzoate, m.p. 89°–91° C.
Butyl 5-acetylamino-2-butoxy-4-nitrobenzoate, m.p. 82°–83° C.
Methyl 4-acetylamino-2-hydroxy-5-nitrobenzoate, m.p. 171°–174° C.
Methyl 4-acetylamino-2-chloro-5-nitrobenzoate, m.p. 132.5°–134° C.

REFERENTIAL EXAMPLE 7

By the procedure of Referential Example 3 the following compounds were prepared from the corresponding alcohols and each acetylaminonitrobenzoate obtained in Referential Examples 2 and 6.
Ethyl 5-amino-2-ethoxy-4-nitrobenzoate, m.p. 140°–141° C.
Butyl 5-amino-2-ethoxy-4-nitrobenzoate, m.p. 90°–92° C.
Methyl 5-amino-4-nitro-2-propoxybenzoate, m.p. 132°–134° C.
Etyhl 5-amino-4-nitro-2-propoxybenzoate, m.p. 101°–102° C.
Propyl 5-amino-4-nitro-2-propoxybenzoate, m.p. 105°–106° C.
Butyl 5-amino-4-nitro-2-propoxybenzoate, m.p. 72°–75° C.
Methyl 5-amino-2-butoxy-4-nitrobenzoate, m.p. 121°–122° C.
Butyl 5-amino-2-butoxy-4-nitrobenzoate, m.p. 67°–68° C.
Methyl 4-amino-2-hydroxy-5-nitrobenzoate, m.p. 197°–199° C.
Methyl 5-amino-2-chloro-4-nitrobenzoate, m.p. 225°–226° C.

REFERENTIAL EXAMPLE 8

5-Amino-2-methoxy-4-nitrobenzoic acid

To a suspension of 13.57 g of methyl 5-amino-2-methoxy-4-nitrobenzoate in 250 ml of dioxane was added a solution of 4.36 g of potassium hydroxide in 25 ml of water, and the mixture was refluxed for 4 hours. To the reaction solution was added 7 ml of concentrated hydrochloric acid. The solvent was evaporated under reduced pressure, and the residue, after addition of dioxane, was refluxed for an hour. The insoluble was removed by filtration, and the filtrate was allowed to stand to give the title compound, m.p. 252°–255° C., yield of 10.99 g.

REFERENTIAL EXAMPLE 9

1-(5-Amino-2-methoxy-4-nitrobenzoyl)pyrrolidine

To a solution of 4.24 g of 5-amino-2-methoxy-4-nitrobenzoic acid in 30 ml of N,N-dimethylformamide was added 3.24 g of N,N'-carbonyldiimidazole at room temperature. After 30 minutes, 5 ml of pyrrolidine was added, and the mixture was stirred for 2 hours. The solvent was evaporated under reduced pressure, and the residue was recrystallized from ethyl acetate to give the title compound, m.p. 159°–162° C., yield of 4.16 g.

REFERENTIAL EXAMPLE 10

By the procedure of Referential Example 9 the following compounds were obtained using dimethylamine and neopentyl alcohol in place of pyrrolidine, respectively.
N,N-Dimethyl 5-amino-2-methoxy-4-nitrobenzamide, m.p. 209°–211° C.
Neopentyl 5-amino-2-methoxy-4-nitrobenzoate, m.p. 173°–177° C.

REFERENTIAL EXAMPLE 11

5-Amino-2-methoxy-4-nitrobenzamide

To a solution of 5.66 g of methyl 5-amino-2-methoxy-4-nitrobenzoate in 200 ml of dioxane was added 50 ml of 28 % ammonia water, and then the mixture was allowed to stand at room temperature for 40 hours. The solvent was evaporated under reduced pressure, and the residue was recrystallized from dioxane to give the title compound, m.p. 250°–257° C., yield of 4.30 g.

REFERENTIAL EXAMPLE 12

N-Ethyl 5-amino-2-methoxy-4-nitrobenzamide

By the procedure of Referential Example 11 the title compound was obtained using a 70 % aqueous ethylamine solution, m.p. 235°–239° C.

REFERENTIAL EXAMPLE 13

Phenyl 5-amino-2-methoxy-4-nitrobenzoate

To a suspension of 5.55 g of 5-amino-2-methoxy-4-nitrobenzoic acid in 40 ml of benzene was added 40 ml of thionyl chloride, and the mixture was refluxed for 4 hours. Subsequently, an excess amount of the thionyl chloride and the solvent were evaporated, the residue was dissolved in 40 ml of benzene, and then 12.3 g of phenol and 15.3 ml of triethylamine were added under ice cooling. The mixture was stirred under ice cooling for 30 minutes and then at room temperature overnight. To the reaction solution were added water and ethyl acetate, the organic layer was washed with 10 aqueous sodium hydroxide solution and water, successively, and then the solvent was evaporated under reduced pressure. The residue was applied on a silica gel column chromatography, and the fractions eluted by benzene were collected and recrystallized from methanol to give the title compound, m.p. 130°–132° C., yield of 2.55 g.

REFERENTIAL EXAMPLE 14

By the procedure of Referential Example 4 the following intermediates of formula III were obtained using the corresponding 5-amino-4-nitrobenzoates in place of methyl 5-amino-2-ethoxy-4-nitrobenzoate.

Ethyl 10-ethoxy-9-ethoxycarbonyl-5-hydroxybenzo[α]-phenazine-6-carboxylate, m.p. 160°–162° C.

Ethyl 9-butoxycarbonyl-10-ethoxy-5-hydroxybenzo[α]-phenazine-6-carboxylate, m.p. 122.5°–123.5° C.

Ethyl 5-hydroxy-9-methoxycarbonyl-10-propoxybenzo[α]-phenazine-6-carboxylate, m.p. 143°–145° C.

Ethyl 9-ethoxycarbonyl-5-hydroxy-10-propoxybenzo[α]-phenazine-6-carboxylate, m.p. 117°–119° C.

Ethyl 5-hydroxy-10-propoxy-9-propoxycarbonylbenzo[α]-phenazine-6-carboxylate, m.p. 153°–155° C.

Ethyl 9-butoxycarbonyl-5-hydroxy-10-propoxybenzo[α]-phenazine-6-carboxylate, m.p. 119°–120° C.

Ethyl 10-butoxy-5-hydroxy-9-methoxycarbonylbenzo[α]-phenazine-6-carboxylate, m.p. 143°–144° C.

Ethyl 10-butoxy-9-butoxycarbonyl-5-hydroxybenzo[α]-phenazine-6-carboxylate, m.p. 122°–124° C.

Ethyl 5-hydroxy-9-methoxycarbonyl-10-methylbenzo[α]-phenazine-6-carboxylate, m.p. 295°–299° C.

REFERENTIAL EXAMPLE 15

Ethyl 5,10-dihydroxy-9-methoxycarbonylbenzo[α]-phenazine-6-carboxylate

By the procedure of Referential Example 4 the title compound was obtained using methyl 4-amino-2-hydroxy-5-nitrobenzoate in place of methyl 5-amino-2-ethoxy-4-nitrobenzoate, m.p. 300° C. or above.

REFERENTIAL EXAMPLE 16

Ethyl 9-ethoxycarbonyl-5-hydroxybenzo[α]phenazine-6-carboxylate

By the procedure of Referential Example 4 the title compound was obtained using ethyl 4-amino-3-nitrobenzoate in place of methyl 5-amino-2-ethoxy-4-nitrobenzoate, m.p. 210°–213° C.

REFERENTIAL EXAMPLE 17

Ethyl 5-hydroxy-10-methoxy-9-phenoxycarbonyl-benzo[α]-phenazine-6-carboxylate

By the procedure of Referential Example 4 the title compound was obtained using phenyl 5-amino-2-methoxy-4-nitrobenzoate in place of methyl 5-amino-2-ethoxy-4-nitrobenzoate, m.p. 171°–173° C.

REFERENTIAL EXAMPLE 18

Ethyl 10-chloro-5-hydroxy-9-methoxycarbonylbenzo[α]phenazine-6-carboxylate

Methyl 5-amino-2-chloro-4-nitrobenzoate in ethanol was reduced with iron - hydrochloric acid, and the resulting crude methyl 4,5-diamino-2-chlorobenzoate was treated by the procedure of Referential Example 4(2) to give the title compound, m.p. 225°–226° C.

REFERENTIAL EXAMPLE 19

Ethyl 9-carboxy-5-hydroxybenzo[α]phenazine-6-carboxylate

By the procedure of Referential Example 4(2) the title compound was obtained using 3,4-diaminobenzoic acid in place of methyl 4,5-diamino-2-ethoxybenzoate, m.p. 300° C. or above

REFERENTIAL EXAMPLE 20

4,5-Diamino-2-methoxybenzamide

A suspension of 3.04 g of 5-amino-2-methoxy-4-nitrobenzamide and 110 mg of 10 % palladium carbon in 300 ml of methanol was stirred at 60° C. under a hydrogen atmosphere. After absorption of hydrogen was completed, the catalyst was removed by filtration, and the filtrate was concentrated to give the title compound, m.p. 181°–183° C., yield of 2.18 g.

REFERENTIAL EXAMPLE 21

N-Ethyl 4,5-diamino-2-methoxybenzamide

By the procedure of Referential Example 20 the title compound was obtained using N-ethyl 5-amino-2-methoxy-4-nitrobenzamide, m.p. 65°–67° C.

REFERENTIAL EXAMPLE 22

Ethyl 5-hydroxy-10-methoxy-9-methoxycarbonyl-benzo[α]phenazine-6-carboxylate (1) To a solution of 2.48 g of ethyl 3-hydroxy-1,4-dihydro1,4-dioxo-2-naphthoate and 1.5 ml of triethylamine in 10 ml of dry tetrahydrofuran was added dropwise 1 ml of ethyl chloroformate at 5° C. or below, and the mixture was stirred at room temperature for 2 hours. The resulting solid was removed by filtration, and the filtrate was evaporated to dryness to give crude ethyl 3-ethoxycarbonyloxy-1,4-dihydro-1,4-dioxo-2-naphthoate.

(2) In 7 ml of N,N-dimethylforamide was dissolved the crude ethyl 3-ethoxycarbonyoxy-1,4-dihydro-1,4-dioxo-2-naphthoate obtained in the above item (1). The resulting solution was added to a solution of 2.16 g of methyl 4,5-diamino-2-methoxybenzoate in 7 ml of N,N-dimethylformamide under ice cooling, and the mixture was stirred for 2 hours Subsequently, 100 ml of ethanol was added, and the resulting crystals were collected by filtration and recrystallized from chloroform - ethanol to give the title compound, m.p. 202.5°–207° C., yield of 3.66 g.

REFERENTIAL EXAMPLE 23

By the procedure of Referential Example 22 the corresponding intermediates of formula III were obtained using ortho phenylenediamines obtained in Referential Examples 20 and 21 in place of methyl 4,5-diamino-2-methoxybenzoate, respectively.

Ethyl 9-carbamoyl-5-hydroxy-10-methoxybenzo[α]-phenazine-6-carboxylate, m.p. 300° C. or above Ethyl 9-ethylcarbamoyl-5-hydroxy-10-methoxybenzo[α]phenazine-6-carboxylate, m.p. 190°–193° C.

REFERENTIAL EXAMPLE 24

Ethyl 5-hydroxy-10-methoxy-9-dimethylcarbamoyl-benzo[α]phenazine-6-carboxylate

A suspension of 3.62 g of N,N-dimethyl 5-amino-2-methoxy4-nitrobenzamide and 150 mg of 10 % palladium carbon in 140 ml of ethanol was stirred at 70°–80° C. under a hydrogen atmosphere. After the absorption of hydrogen was completed, the catalyst was removed by filtration, and the filtrate was evaporated to dryness to give crude N,N-dimethyl 4,5-diamino2-methoxybenzamide, which was then dissolved in 30 ml of tetrahydrofuran.

To the tetrahydrofuran solution under water cooling was added a solution of ethyl 3-ethoxycarbonyloxy-1,4-dihydro-1,4-dioxo-2-naphthoate, obtained by the procedure of Referential Example 22(1) using 3.41 g of ethyl 3-hydroxy-1,4-dihydro-1,4-dioxo-2-naphthoate, in 10 ml of tetrahydrofuran. The mixture was stirred at room temperature for 2 hours. The reaction solution was poured into 100 ml of ethanol, and the resulting crystals were collected by filtration and recrystallized from chloroform - ethanol to give the title compound, m.p. 224°-227° C., yield of 3.70 g.

REFERENTIAL EXAMPLE 25

By the procedure of Referential Example 24 the following intermediates of formula III were obtained using the corresponding ortho nitroanilines in place of N,N-dimethyl 5-amino-2-methoxy-4-nitrobenzamide.

Ethyl 5-hydroxy-10-methoxy-9-(1-pyrrolidinocarbonyl)benzo[α]phenazine-6-carboxylate, m.p. 221°-224° C.

Ethyl 5-hydroxy-10-methoxy-9-neopentyloxycarbonylbenzo[α]phenazine-6-carboxylate, m.p. 153°-157° C.

EXAMPLE 1

N-β-Dimethylaminoethyl 5-hydroxy-10-methoxy-9-methoxycarbonylbenzo[α]phenazine-6-carboxamide To a solution of 20.32 g of ethyl 5-hydroxy-10-methoxy-9 methoxycarbonylbenzo[α]phenazine-6-carboxylate in 500 ml of benzene was added 11 ml of N,N-dimethylethylenediamine, and the mixture was refluxed for 2 hours. The solvent was evaporated under reduced pressure, and the residue was recrystallized from chloroform - ethanol to give the title compound, m.p. 195°-196° C., yield of 22.17 g.

EXAMPLE 2

By the procedure of Example 1 the following compounds of formula I were obtained using the corresponding intermediates of formula III.

N-β-Dimethylaminoethyl 5-hydroxy-9-carboxybenzo[α]phenazine-6 carboxamide, m.p. 245°-246° C.

N-β-Dimethylaminoethyl 9-ethoxycarbonyl-5-hydroxybenzo[α]phenazine-6-carboxamide, m.p. 200°-204° C.

N-β-Dimethylaminoethyl 10-chloro-5-hydroxy-9-methoxycarbonylbenzo[α]phenazine-6-carboxamide, m.p. 217°-221° C.

N-β-Dimethylaminoethyl 5-hydroxy-9-methoxycarbonyl-10methylbenzo[α]phenazine-6-carboxamide, m.p. 219°-220° C.

N-β-Dimethylaminoethyl 5-hydroxy-10-methoxy-9-phenoxycarbonylbenzo[α]phenazine-6-carboxamide, m.p. 189°-190° C.

N-β-Dimethylaminoethyl 5-hydroxy-10-methoxy-9-neopentyloxycarbonylbenzo[α]phenazine-6-carboxamide, m.p. 186°-188° C.

N-β-Dimethylaminoethyl 9-carbamoyl-5-hydroxy-10-methoxybenzo[α]phenazine-6-carboxamide, m.p. 234°-237° C.

N β-Dimethylaminoethyl 9-ethylcarbamoyl-5-hydroxy 10methoxybenzo[α]phenazine-6-carboxamide, m.p. 230°-233° C.

N-β-Dimethylaminoethyl 5-hydroxy-10-methoxy-9-dimethylcarbamoylbenzo[α]phenazine-6-carboxamide, m.p. 202°-204° C.

N-βDimethylaminoethyl 5-hydroxy 10-methoxy-9-(1pyrrolidinocarbonyl)benzo[α]phenazine-6-carboxamide, m.p. 228°-230° C.

N-β-Dimethylaminoethyl 10-ethoxy-5-hydroxy-9-methoxycarbonylbenzo[α]phenazine-6-carboxamide, m.p. 170°-172° C.

N-β-Dimethylaminoethyl 10-ethoxy-9-ethoxycarbonyl-5hydroxybenzo[α]phenazine-6-carboxamide, m.p. 158°-160° C.

N-β-Dimethylaminoethyl 9-butoxycarbonyl-10-ethoxy-5hydroxybenzo[α]phenazine-6-carboxamide, m.p. 138°-140° C.

N-β-Dimethylaminoethyl 5-hydroxy-9-methoxycarbonyl-10propoxybenzo[α]phenazine-6-carboxamide, m.p. 187°-188° C.

N-β-Dimethylaminoethyl 9-ethoxycarbonyl-5-hydroxy-10propoxybenzo[α]phenazine-6-carboxamide, m.p. 154°-155° C.

N-β-Dimethylaminoethyl 5-hydroxy-10-propoxy-9propoxycarbonylbenzo[α]phenazine-6-carboxamide, m.p. 114°-115° C.

N-β-Dimethylaminoethyl 9-butoxycarbonyl-5-hydroxy-10-propoxybenzo[α]phenazine-6-carboxamide, m.p. 65°-66° C.

N-β-Dimethylaminoethyl 10-butoxy-5-hydroxy-9-methoxycarbonylbenzo[α]phenazine-6-carboxamide, m.p. 171°-172° C.

N-β-Dimethylaminoethyl 10-butoxy-9-butoxycarbonyl-5-hydroxybenzo[α]phenazine 6-carboxamide, m.p. 102°-104° C.

N-β-Dimethylaminoethyl 5,10-dihydroxy-9-methoxycarbonylbenzo[α]phenazine-6-carboxamide, m.p. 250° C. (decomposition)

EXAMPLE 3

N-β-Ethylaminoethyl 5-hydroxy-10-methoxy-9-methoxcarbonylbenzo[α]phenazine-6-carboxamide By the procedure of Example 1 the title compound was obtained using N-ethylethylenediamine in place of N,N-dimethylethylenediamine, m.p. 140°-142° C.

EXAMPLE 4

N-β-Diethylaminoethyl 5-hydroxy-10-methoxy-9-methoxycarbonylbenzo[α]phenazine-6-carboxamide By the procedure of Example 1 the title compound was obtained using N,N-diethylethylenediamine in place of N,N-dimethylethylenediamine, m.p. 164°-165° C.

EXAMPLE 5

N-γ-Dimethylaminopropyl 5-hydroxy-10-methoxy-9-methoxycarbonylbenzo[α]phenazine-6-carboxamide By the procedure of Example 1 the title compound was obtained using N,N-dimethylpropylenediamine in place of N,N-dimethylethylenediamine, m.p. 143°-145° C.

EXAMPLE 6

N-β-Dimethylaminoethyl 9-butoxycarbonyl-5-hydroxy-10-methoxybenzo[α]phenazine-6-carboxamide In 400 ml of n-butanol containing 8 ml of concentrated sufluric acid was suspended 21.52 g of N-β-dimethylaminoethyl 5-hydroxy-10-methoxy-9-methoxycarbonylbenzo[α]phenazine-6-carboxamide obtained in Example 1, and the suspension was refluxed for 5 hours. The n-butanol was evaporated under reduced pressure. The residue was poured into an aqueous sodium bicarbonate solution, and the resulting solid was collected by filtration and recrytstallized from chloroformethanol to give the title compound, m.p. 171°–174° C., yield of 21.41 g.

EXAMPLE 7

By the procedure of Example 6 the following corresponding compounds of formula I.were obtained using other alcohols in place of n-butanol.

N-β-Dimethylaminoethyl 9-ethyoxycarbonyl-5-hydroxy-10-methoxybenzo[α]phenazine-6-carboxamide, m.p. 171°–174° C.

N-β-Dimethylaminoethyl 5-hydroxy-10-methoxy-9-propoxycarbonylbenzo[α]phenazine-6-carboxamide, m.p. 164°–166° C.

N-β-Dimethylaminoethyl 9-cyclopentyloxycarbonyl-5-hydroxy-10-methoxybenzo[α]phenazine-6-carboxamide, m.p. 155°–158° C.

N-β-Dimethylaminoethyl 9-hexyloxycarbonyl-5-hydroxy-10-methoxybenzo[α]phenazine-6-carboxamide, m.p. 95°–96° C.

N-β-Dimethylaminoethyl 9-cyclohexyloxycarbonyl-5-hydroxy10-methoxybenzo[α]phenazine-6-carboxamide, m.p. 155°–158° C.

N-β-Dimethylaminoethyl 9-heptyloxycarbonyl-5-hydroxy-10methoxybenzo[α]phenazine-6-carboxamide, m.p. 88°–89° C.

N-β-Dimethylaminoethyl 5-hydroxy-10-methoxy-9-octyloxycarbonylbenzo[α]phenazine-6-carboxamide, m.p. 98°–103° C.

N-β-Dimethylaminoethyl 9-decyloxycarbonyl-5-hydroxy-10methoxybenzo[α]phenazine-6-carboxamide, m.p. 97°–100° C.

N-β-Dimethylaminoethyl 5-hydroxy-10-methoxy-9-pentadecyloxycarbonylbenzo[α]phenazine-6-carboxamide, m.p. 96°–98.5° C.

N-β-Dimethylaminoethyl 9-benzyloxycarbonyl-5-hydroxy-10-methoxybenzo[α]phenazine-6-carboxamide, m.p. 125°–127° C.

EXAMPLE 8

N-β-Dimethylaminoethyl 5-hydroxy-10-methoxy-9-methylcarbamoylbenzo[α]phenazine-6-carboxamide In 900 ml of dioxane was dissolved 2.24 g of N-βdimethylaminoethyl 5-hydroxy-10-methoxy-9-methoxycarbonylbenzo[α]phenazine-6-carboxamide obtained in Example 1, and 100 ml of a 40 % aqueous methylamine solution was added. After allowing to stand at room temperature for 6 days, the reaction solution was evaporated to dryness under reduced pressure, and the residue was recrystallized from chloroform - ethanol to give the title compound, m.p. 245°–248° C., yield of 2.00 g.

EXAMPLE 9

By the procedure of Example 8 the following compounds were obtained using other amines in place of methylamine.

N-β-Dimethylaminoethyl 5-hydroxy-10-methoxy-9-propylcarbamoylbenzo[α]phenazine-6-carboxamide, m.p. 224°–226.5° C.

N-β-Dimethylaminoethyl 9-butylcarbamoyl-5-hydroxy-10methoxybenzo[α]phenazine-6-carboxamide, m.p. 221°–224° C.

EXAMPLE 10

N-β-Dimethylaminoethyl 5-hydroxy-9-methoxycarbonylbenzo-[α]phenazine-6-carboxamide In 100 ml of methanol was suspended 1.45 g of N-β-dimethylaminoethyl 9-carboxy-5-hydroxybenzo[β]-phenazine-6-carboxamide obtained in Example 2 , and an excess amount of diazomethane in ether was added. The reaction mixture was evaporated to dryness under reduced pressure. The residue was applied on a silica gel column chromatography and the fractions eluted by chloroform - methanol (10:1) were collected and recrystallized from methanol to give the title compound, m.p. 200°–203° C., yeild of 0.71 g.

EXAMPLE 11

[α]phenazine-6-carboxamide

In 80 ml of methanol was suspended 4.48 g of N-β-dimethylaminoethyl 5-hydroxy-10-methoxy-9-methoxycarbonylbenzo[α]phenazine-6-carboxamide obtained in Example 1, a solution of 1.18 g of potassium hydroxide in 80 ml of water was added, and the mixture was refluxed for 5 hours. To this were added 350 ml of water and solid carbon dioxide, and the resulting crystals were collected by filtration, dried and recrystallized from N,N-dimethylformamide - ethanol to give the title compound, m.p. 232°–237° C., yield of 3.90 g.

What is claimed is

1. Benzo[α]phenazine derivatives of the formula

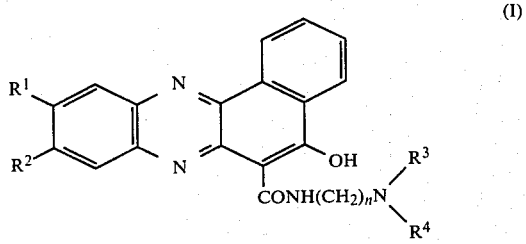

wherein $R^1$ is hydrogen, halogen, methyl, hydroxyl or alkoxy, $R^2$ is —$COOR^5$ (wherein $R^5$ is hydrogen, straight or branched chain alkyl, cycloalk-yl having 3–6 carbon atoms, benzyl or phenyl) or

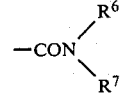

(wherein $R^6$ and $R^7$ are the same or different and are each hydrogen or lower alkyl, or $R^6$ and $R^7$ together with the nitrogen atom to which they are attached form pyrrolidine or piperidine), $R^3$ and $R^4$ are the same or different and are each hydrogen or lower alkyl, and n is an integer of 2 or 3, and the salts thereof.

2. A compound according to claim 1 wherein R wherein $R^1$ is alkoxy, $R^2$ is —$COOR^5$ (wherein $R^5$ is hydrogen or alkyl having 1–6 carbon atoms), $R^3$ and $R^4$ are each methyl, and n is an integer of 2.

3. N-β-Dimethylaminoethyl 9-carboxy-5-hydroxy-10-methoxybenzo[α]phenazine-6-carboxamide 4. N-β-Dimethylaminoethyl 5-hydroxy-10-methoxy-9-methoxycarbonylbenzo[α]phenazine-6-carboxamide 5. N-β-Dimethylaminoethyl 9-butoxycarbonyl-5-hydroxy-10-methoxybenzo[α]phenazine-6-carboxamide 6. N-β-Dimethylaminoethyl 5-hydroxy-9-isopentyloxycarbonyl-10-methoxybenzo[α]phenazine-6-carboxamide

* * * * *

UNITED STATES PATENT AND TRADEMARK OFFICE
CERTIFICATE OF CORRECTION

PATENT NO. : 4,686,292

DATED : August 11, 1987

INVENTOR(S) : Yoshihiro MIGITA; Tadashi EGUCHI; Yukinari KUMAZAWA; Jozi NAKAGAMI; Takehiro AMANO; Kaoru SOTA; Jinsaku SAKAKIBARA It is certified that error appears in the above-identified patent and that said Letters Patent is hereby corrected as shown below:

Col. 2, line 1, delete "wherein"; and line 2, delete "R".

Col. 3, line 18, "trietylamine" should read -- triethylamine --.

Col. 4, line 62, "1 5" should read -- 1.5 --.

Col. 5, line 14, "dihydrol,4-dioxo-2-naphthoate" should read

-- dihydro-1,4-dioxo-2-naphthoate --; and line 57 "Etyhl" should read -- Ethyl --.

Col. 7, line 3, "chromatography" should read -- chromatograph --.

Col. 8, line 26, "dihydrol,4-dioxo-2-naphthoate" should read

-- dihydro-1,4-dioxo-2-naphthoate --;

line 35, "3-ethoxycarbonyoxy-1,4-dihydro-1,4-"

should read -- 3-ethoxycarbonyloxy-1,4-dihydro-1,4- --;

line 40, "hours subsequently" should read -- hours.

Subsequently --;

line 61, "methoxy4-nitrobenzamide should read

-- methoxy-4-nitrobenzamide --; and

UNITED STATES PATENT AND TRADEMARK OFFICE
CERTIFICATE OF CORRECTION

PATENT NO. : 4,686,292

DATED : August 11, 1987

INVENTOR(S) : Yoshihiro MIGITA; Tadashi EGUCHI; YUKINARI KUMAZAWA;
Jozi NAKAGAMI; Takehiro AMANO; Kaoru SOTA; Jinsaku SAKAKIBARA It is certified that error appears in the above-identified patent and that said Letters Patent is hereby corrected as shown below:

line 66, "4,5-diamino2-methoxyben-" should read

-- 4,5-diamino-2-methoxyben- --.

Col. 9, line 51, "bonyl-10methylbenzo[α]phenazine-6-carboxamide"

should read -- bonyl-10-methyl-benzo[α]phenazine-6- carboxamide --; and line 63, "N β-Dimethylaminoethyl" should read

-- N-β-Dimethylaminoethyl --.

Col. 10, line 2, "(1pyrrolidinocarbonyl)benzo[α]phenazine-6-carboxa-"

should read -- (1-pyrrolidinocarbonyl)benzo[α]phenazine-6- carboxa- --;

line 8, "nyl-5hydroxybenzo[α]phenazine-6-carboxamide" should read

-- nyl-5-hydroxybenzo[α]phenazine-6-carboxamide --;

line 11, "ethoxy-5hydroxybenzo[α]phenazine-6-carboxamide,"

should read -- ethoxy-5-hydroxybenzo[α]phenazine-6- carboxamide, --;

UNITED STATES PATENT AND TRADEMARK OFFICE
CERTIFICATE OF CORRECTION

PATENT NO. : 4,686,292

DATED : August 11, 1987

INVENTOR(S) : Yoshihiro MIGITA; Tadashi EGUCHI; Yukinari KUMAZAWA; Jozi NAKAGAMI; Takehiro AMANO; Kaoru SOTA; Jinsaku SAKAKIBARA It is certified that error appears in the above-identified patent and that said Letters Patent is hereby corrected as shown below:

line 14, "bonyl-10propoxybenzo[α]phenazine-6-carboxamide,"

should read -- bonyl-10-propoxybenzo[α]phenazine-6-carboxamide, --;

line 17, "hydroxy-10propoxybenzo[α]phenazine-6-carboxamide" should read -- hydroxy-10-propoxybenzo[α]phenazine-6-carboxamide, --;

line 20, "9propoxycarbonylbenzo[α]phenazine-6-carboxamide," should read -- 9-propoxycarbonylbenzo[α]phenazine-6-carboxamide, --; and line 37, "methoxcarbonylbenzo[α]phenazine-6-carboxamide" should read -- methoxycarbonylbenzo[α]phenazine-6-carboxamide --.

Col. 11, line 1, "recrytstallized" should read -- recrystallized --;

lines 16-25 should read

-- N-β-Dimethylaminoethyl 5-hydroxy-10-methoxy-9-isopropoxycarbonylbenzo[α]phenazine-6-carboxamide, m.p. 162 - 163 °C

UNITED STATES PATENT AND TRADEMARK OFFICE
CERTIFICATE OF CORRECTION

PATENT NO. : 4,686,292

DATED : August 11, 1987

INVENTOR(S) : Yoshihiro MIGITA; Tadashi EGUCHI; Yukinari KUMAZAWA;
Jozi NAKAGAMI: Takehiro AMANO; Kaoru SOTA; Jinsaku SAKAKIBARA It is certified that error appears in the above-identified patent and that said Letters Patent is hereby corrected as shown below:

N-β-Dimethylaminoethyl 9-isobutoxycarbonyl-5-hydroxy-10-methoxybenzo[α]phenazine-6-carboxamide, m.p. 149 - 151 °C N-β-Dimethylaminoethyl 5-hydroxy-10-methoxy-9-pentyloxycarbonylbenzo[α]phenazine-6-carboxamide, m.p. 119 - 120 °C N-β-Dimethylaminoethyl 5-hydroxy-10-methoxy-9-isopentyloxycarbonylbenzo[α]phenazine-6-carboxamide, m.p. 140 - 143 °C N-β-Dimethylaminoethyl 9-cyclopentyloxycarbonyl-5-hydroxy-10-methoxybenzo[α]phenazine-6-carboxamide, m.p. 155-158 °C N-β-Dimethylaminoethyl 9-hexyloxycarbonyl-5-hydroxy-10-methoxybenzo[α]phenazine-6-carboxamide, m.p. 95 - 96 °C N-β-Dimethylaminoethyl 9-cyclohexyloxycarbonyl-5-hydroxy-10-methoxybenzo[α]phenazine-6-carboxamide, m.p. 155 - 158 °C --;
and line 27, "hydroxy-10methoxybenzo[α]phenazine-6-carboxamide," should read -- hydroxy-10-methoxybenzo[α]phenazine-6-carboxamide, --.

Col. 12, line 11, "chromatography" should read --chromatograph --;

UNITED STATES PATENT AND TRADEMARK OFFICE
CERTIFICATE OF CORRECTION

PATENT NO. : 4,686,292
DATED : August 11, 1987
INVENTOR(S) : Yoshihiro MIGITA; Tadashi EGUCHI; YUKINARI KUMAZAWA; Jozi NAKAGAMI; Takehiro AMANO; Kaoru SOTA; Jinsaku SAKAKIBARA It is certified that error appears in the above—identified patent and that said Letters Patent is hereby corrected as shown below:

line 14, "yeild" should read -- yield --;

line 16, should read

-- N-β-Dimethylaminoethyl 9-carboxy-5-hydroxy-10-methoxy-benzo[α]phenazine-6-carboxamide --;

line 42, "cycloalk-yl" should read -- cycloalkyl --; and line 55, delete "wherein R".

Signed and Sealed this

First Day of March, 1988

Attest:

DONALD J. QUIGG

Attesting Officer

Commissioner of Patents and Trademarks